(12) United States Patent
Hourmand et al.

(10) Patent No.: US 9,446,196 B2
(45) Date of Patent: Sep. 20, 2016

(54) AUTO-INJECTOR

(75) Inventors: Yannick Hourmand, Haslingfield (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 747 days.

(21) Appl. No.: 13/993,533

(22) PCT Filed: Dec. 21, 2011

(86) PCT No.: PCT/EP2011/073504
§ 371 (c)(1),
(2), (4) Date: Jun. 12, 2013

(87) PCT Pub. No.: WO2012/085023
PCT Pub. Date: Jun. 28, 2012

(65) Prior Publication Data
US 2013/0267898 A1   Oct. 10, 2013

(30) Foreign Application Priority Data

Dec. 21, 2010   (EP) .................................... 10196069

(51) Int. Cl.
| | | |
|---|---|---|
| A61M 5/32 | (2006.01) | |
| A61M 5/315 | (2006.01) | |
| A61M 5/20 | (2006.01) | |
| A61M 5/31 | (2006.01) | |

(52) U.S. Cl.
CPC ........... *A61M 5/2033* (2013.01); *A61M 5/326* (2013.01); *A61M 5/3257* (2013.01); *A61M 2005/206* (2013.01); *A61M 2005/208* (2013.01); *A61M 2005/3143* (2013.01)

(58) Field of Classification Search
CPC ................... A61M 2005/206; A61M 5/2033; A61M 5/326; A61M 2005/208; A61M 2005/2013; A61M 5/3287; A61M 5/3202; A61M 5/3204; A61M 5/3272; A61M 5/50; A61M 2005/3143; A61M 5/3257
See application file for complete search history.

(56) References Cited

U.S. PATENT DOCUMENTS

| 9,283,327 B2 * | 3/2016 | Hourmand .......... A61M 5/2033 |
| 2002/0095120 A1 | 7/2002 | Larsen et al. |

(Continued)

FOREIGN PATENT DOCUMENTS

| GB | 2463071 | 3/2010 |
| WO | 2006/057604 | 6/2006 |

OTHER PUBLICATIONS

International Search Report for Int. App. No. PCT/EP2011/073504, completed Jan. 31, 2012.

*Primary Examiner* — Kevin C Sirmons
*Assistant Examiner* — William Carpenter
(74) *Attorney, Agent, or Firm* — Fish & Richardson P.C.

(57) ABSTRACT

An auto-injector comprises a chassis to contain a syringe with a, needle and a stopper, a needle shroud slideable within the chassis and adapted to rest on the skin of a patient, a plunger adapted to translate the stopper to expel medicament, a coupling shroud slideable within the chassis and releasably coupled to the plunger and a drive means, the drive means driving the coupling shroud proximally from a first position Proximal movement of the coupling shroud translates the syringe exposing the needle, depresses the plunger to expel medicament and advances the needle shroud to a safe position to surround the needle. The needle shroud arranged to prevent decoupling of plunger and coupling shroud when the needle shroud is in a retracted position, whereas the needle shroud is arranged to allow decoupling of plunger and coupling shroud when the needle shroud is moved towards the safe position.

13 Claims, 3 Drawing Sheets

(56) References Cited

U.S. PATENT DOCUMENTS

2006/0224124 A1* 10/2006 Scherer ............... A61M 5/2033
                                                          604/220
2008/0262436 A1* 10/2008 Olson ................. A61M 5/2033
                                                          604/198
2013/0274662 A1* 10/2013 Hourmand .......... A61M 5/2033
                                                          604/110

* cited by examiner

AUTO-INJECTOR

CROSS REFERENCE TO RELATED APPLICATIONS

The present application is a U.S. National Phase Application pursuant to 35 U.S.C. §371 of International Application No. PCT/EP2011/073504 filed Dec. 21, 2011, which claims priority to European Patent Application No. 10196069.8 filed Dec. 21, 2010 and U.S. Provisional Patent Application No. 61/432,252 filed Jan. 13, 2011. The entire disclosure contents of these applications are herewith incorporated by reference into the present application.

TECHNICAL FIELD

The invention relates to an auto-injector for administering a dose of a liquid medicament.

BACKGROUND

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Injection forces/button extension, hand-shaking and the likelihood of delivering an incomplete dose are reduced. Triggering may be performed by numerous means, for example a trigger button or the action of the needle reaching its injection depth. In some devices the energy to deliver the fluid is provided by a spring.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, torsion stored in the tension spring is released and the injection needle is automatically retracted back to its original storage position.

SUMMARY

It is an object of the present invention to provide an improved auto-injector.

The object is achieved by an auto-injector according to claim 1.

Preferred embodiments of the invention are given in the dependent claims.

In the context of this specification, the terms distal and proximal are defined from the point of view of a person receiving an injection. Consequently, a proximal direction refers to a direction pointing towards the body of a patient receiving the injection and a proximal end defines an end of an element that is directed towards the body of the patient. Respectively, the distal end of an element or the distal direction is directed away from the body of the patient receiving the injection and opposite to the proximal end or proximal direction.

According to the invention, an auto-injector for administering a dose of a liquid medicament comprises a substantially cylindrical chassis arranged to contain a pre-filled syringe with a syringe barrel filled with the medicament, an injection needle and a stopper for sealing the syringe barrel, a needle shroud slidably arranged within the chassis and adapted to rest on the skin of a patient receiving an injection, a plunger adapted to translate the stopper to expel the dose of the medicament through the injection needle, a coupling shroud slidably arranged within the chassis and releasably coupled to the plunger and a drive means. Upon release, the drive means is capable of driving the coupling shroud from a first position in a proximal direction. The proximal translatory movement of the coupling shroud with respect to the chassis translates the pre-filled syringe in the proximal direction to expose the injection needle, depresses the plunger connected to the stopper into the syringe barrel to expel the dose of medicament and advances the needle shroud to a safe position to surround the injection needle after the injection. The coupling shroud is arranged to be decoupled from the plunger at a second position. The needle shroud is arranged to prevent the decoupling of plunger and coupling shroud when the needle shroud is in a refracted position, whereas the needle shroud is arranged to allow for the decoupling of plunger and coupling shroud when the needle shroud is moved from the retracted position towards the safe position.

A crucial step in delivering medicaments with auto-injectors is the decoupling of the plunger at the appropriate point in time. If the plunger is decoupled early, the dose of the medicament might not be completely expelled. Consequently the medicament is partially wasted during the injection. However, such an early release might be necessary to ensure that the plunger is decoupled at the end of an injection stroke, so that in particular functions that ensure needle safety are reliably carried out. The injection mechanism of the auto-injector is designed in a manner that allows for a complete emptying of the syringe barrel containing the dose of the medicament before the plunger is decoupled from the coupling shroud without compromising needle safety. During the injection, the needle shroud of the auto-injector is pushed against an injection site as to move the needle shroud into the retracted position. The needle shroud is arranged to prevent the decoupling of the plunger from the coupling shroud as long as the needle shroud remains in the retracted position. When the dose of the medicament has been completely expelled and the auto-injector is removed from the injection site, the needle shroud leaves the retracted position and is moved proximally towards the safe position. Thus, the auto-injector according to the invention provides a reliable mechanism that covers the injection needle to avoid accidental needle stick injuries after the injection without wasting any medicament initially contained in the pre-filled syringe.

Preferably, the coupling shroud is initially coupled to the plunger to translate the syringe retainer proximally, whereby the injection needle is inserted into the skin of the patient, and to subsequently depress the stopper into the syringe barrel to expel the medicament. A coupling catch of the coupling shroud abutting against a shoulder formed to the plunger provides a particular simple and reliable means to releasably couple the plunger to the coupling shroud. The coupling catch and the shoulder is arranged in a ramped engagement with each other as to allow for a deflection of the coupling catch in a radial outward direction when the coupling shroud is translated with respect to the plunger in the proximal direction, whereby the coupling between the plunger and the coupling shroud is released. A premature decoupling of the plunger and the coupling shroud is prevented as the coupling catch abuts against the chassis in the radial outward direction until the coupling shroud reaches the second position.

According to a possible embodiment of the invention, the decoupling of the plunger and the coupling shroud takes place at the second position that is located in a manner, so that the needle shroud may be advanced by the decoupled coupling shroud that is biased by the drive means after the stopper has bottomed out and the medication has been completely delivered. The second position is defined by an aperture in the chassis.

The aperture formed into the chassis at the second position allows the coupling catch to deflect radially outwards at the second position, so that the coupling shroud is decoupled from the plunger after the medicament is completely delivered and the auto injector is removed from the injection site.

Preferably, the needle shroud comprises an intermediate section that is slidably retained within the aperture formed into the chassis. When the needle shroud is located in the retracted position, the intermediate section of the needle shroud abuts against the coupling catch in the radial direction. Thus the decoupling of the plunger from the coupling shroud is prevented until the needle shroud leaves the retracted position. As the auto-injector is pushed against the skin of the patient during the injection to retain the needle shroud in the refracted position, the needle shroud cannot leave the retracted position until the auto-injector is removed from the injection site. Thus, the decoupling is delayed until the dose of the medication contained in the pre-filled syringe is completely expelled and the auto-injector is removed from the injection site before the needle safety features of the auto-injector are activated.

According to another possible embodiment of the invention, a syringe retainer is slidably arranged with respect to the chassis. The syringe retainer receives and mounts the pre-filled syringe to the chassis of the auto-injector, wherein initially the syringe retainer is releasably affixed to the chassis. The needle shroud in the retracted position releases the syringe retainer to allow for the proximal translation of the syringe retainer with respect to the chassis. Thus, a proximal movement of the syringe retainer that inserts the injection needle into the skin of the patient is prevented until the auto-injector is correctly placed upon the skin of the patient and the needle shroud is pushed against the skin surface towards the retracted position. This prevents an inadvertent early initiation of the injection and accidental needle stick injuries resulting from an inaccurate placement of the auto-injector.

According to yet another possible embodiment of the invention, the drive means is arranged as a single compression spring. The mechanism of the auto-injector is arranged in a manner that a plurality of functions is executed by the single drive means. The injection needle is inserted into the skin of the patient, the plunger is translated to expel the medicament and the needle shroud is moved proximally to provide needle safety after the injection is completed by the action of the drive means. Conventional auto-injectors usually comprise a plurality of spring means to accomplish these tasks. The auto-injector according to the invention comprises only few parts and is particularly inexpensive to mass-produce. Consequently, the auto-injector is particularly suited as a single-use device that may be disposed after an injection has been carried out.

According to yet another possible embodiment of the invention, a manually actuatable and tubular release element is slideably arranged with respect to the chassis. Manual actuation of the release element releases the drive means and initiates the injection. The tubular release element extends over a substantial length of the chassis and may easily be gripped by a user carrying out the injection. Alternatively, the release element may be arranged as a push button at a distal end of the auto-injector. The auto-injector is particularly intuitive to operate.

According to an alternative embodiment of the invention, the release element is hinged to a lateral side of the chassis. Conventional auto-injectors are commonly activated by actuating a push button or the like arranged at a distal end of the auto-injector. An inexperienced user of such a conventional auto-injector may easily mistake the distal end for a proximal end of the auto-injector and thus may pierce his finger while trying to actuate the auto-injector. The lateral arrangement of the release element is a simple means to prevent such accidental needle stick injuries resulting from a misuse of the auto-injector.

According to yet another embodiment of the invention, the release element is initially latched to the chassis to prevent an inadvertent manual actuation releasing the drive means. Pushing the needle shroud against the skin of the patient moves the needle shroud in the retracted position. The needle shroud in the retracted position is arranged to unlatch the release element, so that the release element may be manually actuated to release the drive means. This forces the user of the auto-injector to perform a series of actions necessary to start the injection in the proper order to minimize the risk of needle stick injuries and/or an inadvertent release of the drive means expelling the medicament. In particular, the auto-injector first has to be properly placed onto the skin of the person before the injection needle is inserted by actuating the release element.

In one possible embodiment of the invention, a resilient bushing is arranged to engage the coupling shroud that is biased by the drive means and coupled to the plunger of the pre-filled syringe. The elastic bushing is firmly attached to a distal end of the chassis. The coupling shroud initially latches to the bushing to prevent an inadvertent and early release of the drive means.

According to yet another possible embodiment of the invention, the needle shroud is slidable from an initial advanced position in a distal direction to a retracted position. In particular, the needle shroud may be slid to the retracted position by placing the auto-injector onto the skin of the patient receiving the injection and pressing the needle shroud against the skin of the patient. The needle shroud in the retracted position indicates the correct placement of the auto-injector. An activation of the mechanism of the auto-injector delivering the medicament to the patient requires the needle shroud to be positioned in the retracted position to ensure that the auto-injector is properly used. The needle shroud is slidable from the retracted position in the proximal direction beyond the advanced position and further to the safe position. In the safe position, the needle shroud surrounds the injection needle of the pre-filled syringe to prevent accidental needle stick injuries after the injection has been carried out.

In another possible embodiment of the invention, a rotating collar is arranged within the chassis of the auto-injector and axially fixed to the chassis as to prevent an axial translation of the rotating collar in at least the proximal direction. The rotating collar engages the needle shroud in a manner that forces the rotating collar to rotate within the chassis when the needle shroud is axially displaced, and, in particular, translated in the proximal direction. The rotating collar creates friction to slow down the proximal movement of the needle shroud that rests on the skin of the patient during the injection. The rotating collar acts as a dampening element that alleviates the pressure exerted upon the skin of the patient by the needle shroud. Thus, the risk of injuries is reduced and, in particular, bruises may be avoided. Furthermore, the modulus of resilience of the drive means driving the needle shroud may be chosen to be sufficiently large without having to worry about potential injury risks. Thus, the modulus of resilience of the drive means is adapted to reliably provide an energy supply for executing a plurality of actions comprising, among others, the advancing and releasing of the needle shroud, the displacement of the stopper to expel the medicament and the decoupling of the plunger from the coupling shroud.

Preferably, the rotating collar comprises a pin that engages a helical recess formed into the needle shroud. The engagement of the helical recess and the pin forces the rotating collar to rotate around the needle shroud when the needle shroud is translated from the advanced position to the safe position. This dampens the proximal movement of the needle shroud and thus reduces impact upon the skin of the patient by generating friction.

The auto-injector may preferably be used for subcutaneous or intra-muscular injection, particularly for delivering one of an analgetic, an anticoagulant, insulin, an insulin derivate, heparin, Lovenox, a vaccine, a growth hormone, a peptide hormone, a protein, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION

Figure 1A:
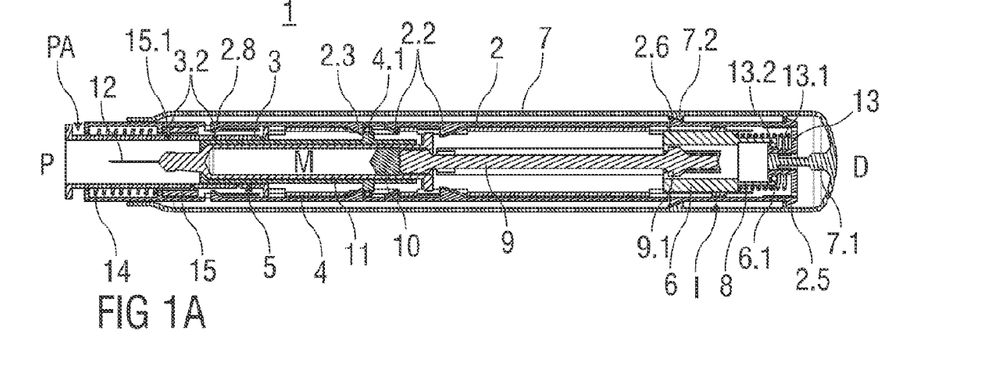
FIGS. 1A and 1B show two different sectional views of the auto-injector before an injection.
Figure 1B:
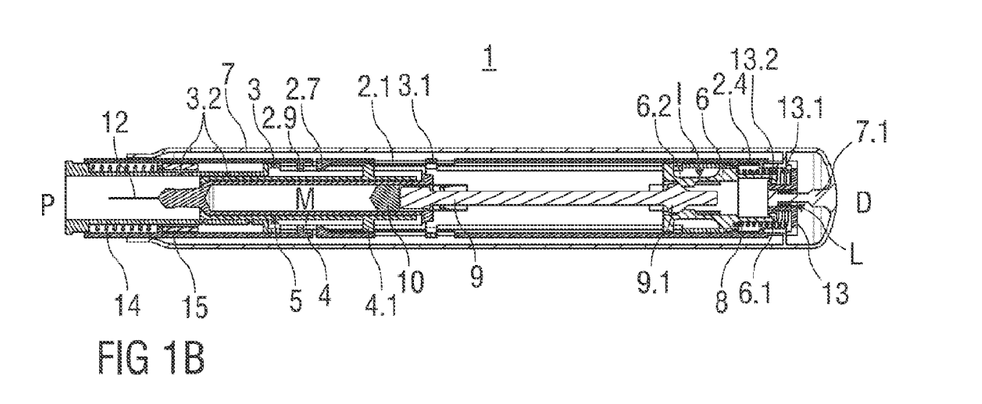

FIGS. 1A and 1B show two sectional views of an essentially cylindrical auto-injector 1, wherein the sectional planes shown are oriented perpendicularly to each other. The auto-injector 1 comprises a chassis 2, a needle shroud 3, a syringe retainer 4 adapted to mount a pre-filled syringe 5 within the chassis 2 and a coupling shroud 6 slidably arranged within the chassis 2. A tubular release element 7 is in slidable arrangement with the cylindrical chassis 2 and may be gripped by a user performing an injection. The tubular release element 7 and the needle shroud 3 extend over a substantial axial length of the chassis 2.

Alternatively, the release element 7 may be arranged as a push button located at a distal end of the auto-injector 1.

In another alternative embodiment of the invention, the release element 7 is laterally hinged to the chassis 2 and may pivot about a hinge to activate the injection mechanism of the auto-injector 1.

A single drive means 8 is arranged within the chassis 2 to bias the coupling shroud 6 in a proximal direction P towards the skin of a patient receiving an injection.

According to one possible embodiment of the invention, the drive means 8 is arranged as a single, conventional compression spring.

The coupling shroud 6 is releasably coupled to a plunger 9 connected to a stopper 10 fluid-tightly sealing a distal end of a syringe barrel 11 containing a dose of a medicament M. An inner cavity of the syringe barrel 11 is in fluid communication with an injection needle 12, so that the dose of the medicament M may be expelled through the injection needle 12 by displacing the stopper 10 in the proximal direction P.

A bushing 13 is firmly attached to the distal end of the chassis 2. The bushing 13 comprises a resilient inner sleeve 13.1 with a collar 13.2 that protrudes radially outwards. A lug 7.1 formed to an inner surface of the release element 7 is retained within the inner sleeve 13.1 in a locked position L. The lug 7.1 snugly fits into the inner sleeve 13.1, so that a deformation and an inward deflection of the inner sleeve 13.1 are prevented.

Furthermore, the bushing 13 acts as a counter bearing for the drive means 8 to bias the coupling shroud 6 in the proximal direction P.

A first clip 6.1 is formed to the coupling shroud 6 that latches to the collar 13.2 of the bushing 13 to releasably retain the coupling shroud 6 in a first position I, wherein the coupling shroud 6 is located at a distal end of the chassis 2 and the drive means 8 is fully compressed, so that the coupling shroud 6 is strongly biased in the proximal direction P.

The plunger 9 extends from the syringe barrel 11 in a distal direction D and comprises a shoulder 9.1 with an increased diameter. The coupling shroud 6 comprises an inwardly protruding coupling catch 6.2 that abuts against the shoulder 9.1 so that the plunger 9 and the coupling shroud 6 may be jointly moved in the proximal direction P by the action of the relaxing drive means 8. An inner surface of the chassis 2 abuts radially against the coupling catch 6.2 to prevent an outward deflection thereof. A longitudinal aperture 2.1 is formed into the chassis 2 to allow for a radial outward deflection of the coupling catch 6.1 at the end of an injection stroke, so that the coupling catch 6.1 may overcome the shoulder 9.1 to decouple the coupling shroud 6 and the plunger 9 after the medicament M has been delivered.

The needle shroud 3 is designed to rest on the skin surface of the patient during the injection. Edges of the needle shroud 3 may thus be smoothed to avoid injuries. The needle shroud 3 is slidably arranged with the chassis 2 of the auto-injector 1, so that the needle shroud 3 may be pushed from an advanced position PA shown in FIG. 1 in the distal direction D. A biasing means 14 bears against the needle shroud 3 and the chassis 2 to bias the needle shroud towards the advanced position PA. The biasing means 14 may be arranged as a compression spring.

An intermediate section 3.1 of the needle shroud 3 may slide along the longitudinal aperture 2.1 when the needle shroud 3 is axially translated. The coupling catch 6.2 may engage the intermediate section 3.1 of the needle shroud 3 at the end of an injection stroke to prevent an early decoupling of the coupling collar 6 and the plunger 9. (See FIGS. 2 and 4)

A ring-shaped rotating collar 15 is axially fixed to the chassis 2 in the proximal direction P and engages an outer surface of the needle shroud 3. The rotating collar 15 rotates around an axis of the auto-injector 1 when the needle shroud 3 is axially displaced in the proximal direction P. The rotating collar 15 acts as a dampening means that creates friction to slow down the proximal movement of the needle shroud 3 after the medicament M has been delivered beneath the skin of the patient. A helical recess 3.2 is formed into an outer surface of the needle shroud 3 that accommodates a pin 15.1 formed to an inner surface of the rotating collar 14. When the needle shroud 3 is translated with respect to the chassis 2 from an advanced position PA to a safe position PS, the pin 15.1 travels along the helical recess 3.2, so that the rotating collar 14 is forced to rotate within the chassis 2 around the axis of the auto-injector 1.

Before the injection, the needle shroud 3 is mounted to the chassis 2 by retaining protrusions 2.2 that protrude into orifices formed into lateral sides of the needle shroud 3. Each orifice comprises an axial length that is dimensioned to allow the needle shroud 3 to be slid from the advanced position PA to a retracted position PR.

A first catch 2.3 is formed to an inner surface of the chassis 2 and protrudes through an opening formed into the needle shroud 3 to releasably retain the syringe retainer 4 retaining the pre-filled syringe 5. The first catch 2.3 comprises a bevelled ramp and is deflectable in a radial outward direction. The first catch 2.3 latches to an outward protrusion 4.1 formed to the outer surface of the syringe retainer 4 when the needle shroud 3 is in the advanced position PA.

The needle shroud 3 abuts against the bevelled ramp of the first catch 2.3 when the needle shroud 3 is moved from the advanced position PA in the distal direction D, whereby the first catch 2.3 is deflected in a radial outward direction and disengages the outward protrusion 4.1 from the chassis 2, so that the syringe retainer 4 may be moved in the proximal direction P.

Before use of the auto-injector 1, second clips 2.4 on the chassis 2 latch to the release element 7. The second clips 2.4 block the movement of the release element 7 in the proximal direction P, so that a manual actuation of the release element 7 is prevented as long as the needle shroud 3 is in the advanced position PA.

Figure 3A:
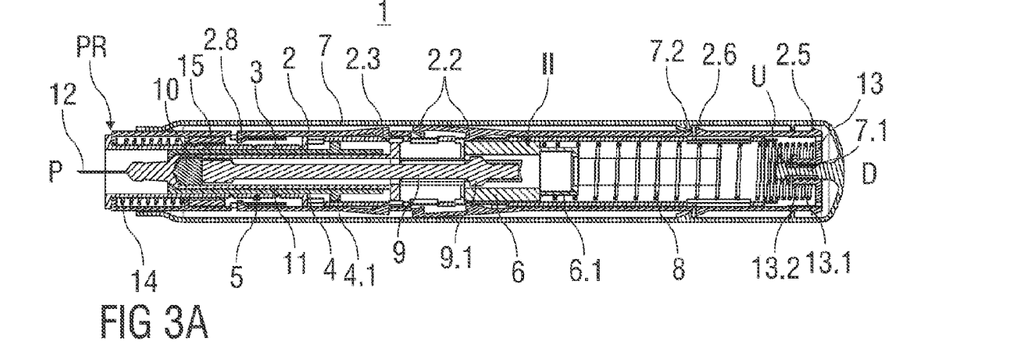
FIGS. 3A and 3B show two different sectional views of the auto-injector after an injection stroke delivering a medicament has been carried out.
Figure 3B:
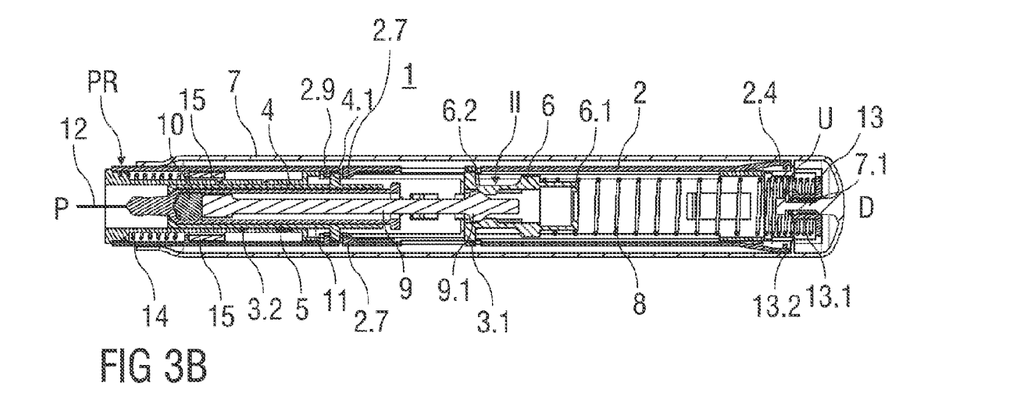

The second clip 2.4 comprises a bevelled ramp that the needle shroud 3 engages when pushed from the advanced position PA in the distal direction D to the refracted position PR, shown in detail in FIGS. 3A and 3B, whereby the second clip 2.4 is radial outwardly deflected to allow for a proximal movement of the release element 7 with respect to the chassis 2. The release element 7 may now be actuated to release the drive means 8.

A distal movement of the release element 7 is blocked by a second catch 2.5 latching to an inner surface of the release element 7.

Additionally, the release element 7 is releasably retained in position before the injection by first and second detents 2.6, 7.2 respectively formed to an outer surface of the chassis 2 and an inner surface of the release element 7, wherein the first and the second detents 2.6, 7.2 comprise correspondingly shaped bevelled ramps facing each other. The first detent 2.6 may deflect radially inwards to overcome the second detent 7.2 when the release element 7 is pushed in proximal direction P.

Figure 2:
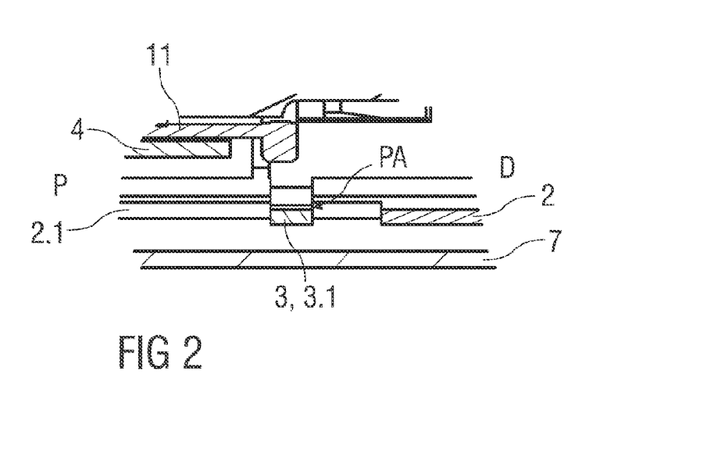
FIG. 2 illustrates details of the auto-injector in a sectional view.

FIG. 2 shows details of the auto-injector 1 in a sectional view. The intermediate section 3.1 of the needle shroud 3 is retained in the longitudinal aperture 2.1. The needle shroud 3 is in the advanced position PA and may slide in the distal direction D towards the retracted position PR, whereby the intermediate section 3.1 moves within the aperture 2.1 towards a distal end thereof.

In order to inject the dose of the medicament M contained in the pre-filled syringe 5, the user of the auto-injector 1 pushes the needle shroud 3 against the skin of the patient to move the needle shroud 3 distally to the retracted position PR illustrated in FIGS. 3A and 3B. The needle shroud 3 moves in the distal direction D and deflects the bevelled ramp of the first catch 2.3 to unlatch the syringe retainer 4. Furthermore, the needle shroud 3 engages the bevelled ramp of the second clip 2.4 and deflects the second clip radial outwardly, so that the release element 7 may be manually actuated to release the drive means 8.

The release means 7 is pushed in the proximal direction P to an unlocked position U, whereby the lug 7.1 disengages the collar 13.2 of the bushing 13. The inner sleeve 13.1 may thus be deformed to release the first clips 6.1 and release the coupling shroud 6 and the drive means 8. Detents 2.6 and 7.2 offer a degree of resistance to the proximal movement of release means 7 as their ramped faces move past each other, This provides a differentiation in the resistance felt by the user between pushing the needle shroud from the advanced to the retracted position, and activating the injection process, thereby improving the experience of the user in using the auto-injector.

Upon release of the drive means 8, the coupling shroud 6 is urged in the proximal direction P. The single and fully charged drive means 8 drives the coupling shroud 6 and the plunger 9 coupled thereto in the proximal direction P. The coupling shroud 6 first pushes the syringe retainer 4 in the proximal direction P until the injection needle 12 of the pre-filled syringe 5 retained within the syringe retainer 4 punctures the skin of the patient. When the injection needle 12 is inserted into the skin of the patient, a third clip 2.7 formed into a lateral side of the chassis 2 latches to the outward protrusion 4.1 of the syringe retainer 4, as illustrated in FIG. 3B, as to prevent a subsequent axial translation of the syringe retainer 4 with respect to the chassis 2.

The protrusion 4.1 abuts against a rib 2.9. in the chassis 2 defining the injection depth of the needle 12. The third clip 2.7 is arranged to hold the protrusion 4.1 in place after it has reached the full injection depth. When the syringe retainer 4 carrying the pre-filled syringe 5 is clipped to the chassis 2 by the third clips 2.7, the injection needle 12 protrudes from the needle shroud 3 in the proximal direction P and penetrates the skin surface of the patient at the desired injection depth.

The coupling shroud 6 is moved by the drive means 8 in the proximal direction P into a second position II illustrated in FIG. 3A. As the syringe retainer 4 and syringe 5 can move no further in the proximal direction, plunger 9 and stopper 10 are forced further into the bore of syringe barrel 11, displacing medicament M through the needle 12. The coupling shroud 6 in the second position II engages a bevelled ramp of the distal retaining protrusion 2.2. The retaining protrusions 2.2 are resiliently supported and may be deflected in the radial outward direction. The coupling shroud 6 engaging the distal retaining protrusion 2.2 pushes the section of the chassis 2 supporting the retaining protrusions 2.2 radially outwards, whereby the needle shroud 3 is released from the chassis 2 and may move towards the advanced position PA and further to the safe position PS upon removal of the auto-injector 1 from the injection site.

Figure 4:
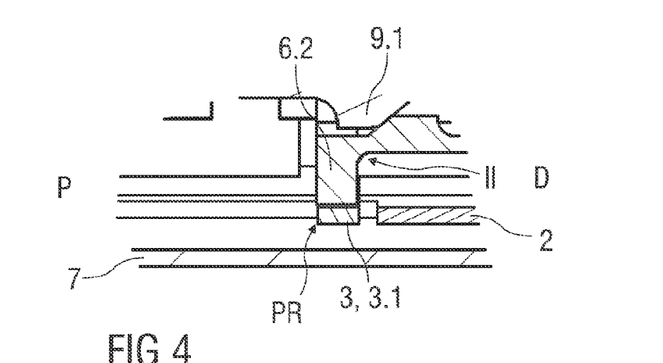
FIG. 4 illustrates details of the auto-injector in a sectional view that ensure a complete delivery of the medication.

As illustrated in detail in FIG. 4, the intermediate section 3.1 of the needle shroud 3 is located near the distal end of the longitudinal aperture 2.1 as long as the needle shroud 3 is retained in the retracted position PR by pushing the needle shroud 3 against the skin of the patient. In a second position II, the coupling catch 6.2 bears against the intermediate section 3.1 in a radial outward direction. An outward deflection of the coupling catch 6.2 releasing the coupling between the plunger 9 and the coupling shroud 6 is thus prevented whilst needle shroud 3 is in the retracted position PR. The user holds the auto-injector against the skin for a sufficient period of time to ensure the plunger 9 is fully depressed in the syringe barrel 11 and the dose of the medicament M is completely expelled.

The auto-injector 1 is then removed from the injection site, whereby the biasing means 14 moves the needle shroud 3 and in particular the intermediate section 3.1 of the needle shroud 3 in the proximal direction P. The coupling catch 6.2 may now protrude into the aperture 2.1 allowing for an outward deflection of the coupling catch 6.2 decoupling the plunger 9 and the coupling shroud 6 due to the ramped engagement of the shoulder 9.1 and the coupling catch 6.2.

As the coupling catch 6.2 is forced radially outwards after the intermediate section 3.1 has moved in the proximal direction P, the coupling catch 6.2 will move out just behind the intermediate section 3.1 and as it is now released from the plunger 9 can push the intermediate section 3.1 and hence the needle shroud 3 in the proximal direction P. The biased coupling shroud 6 bears against the needle shroud 3 and moves the needle shroud 3 from the retracted position PR to the safe position PS shown in FIGS. 5A and 5B. The rotating collar 15 with the pin 15.1 engaging the helical recess 3.2 of the needle shroud 3 rotates while the needle shroud 3 is moved in the proximal direction P. The proximal movement of the needle shroud 3 is thus slowed down and damped. The rotating collar 15 acts as a damping element that reduces impact upon the skin of the patient by the needle shield 3 on translation into the safe position PS.

Figure 5A:
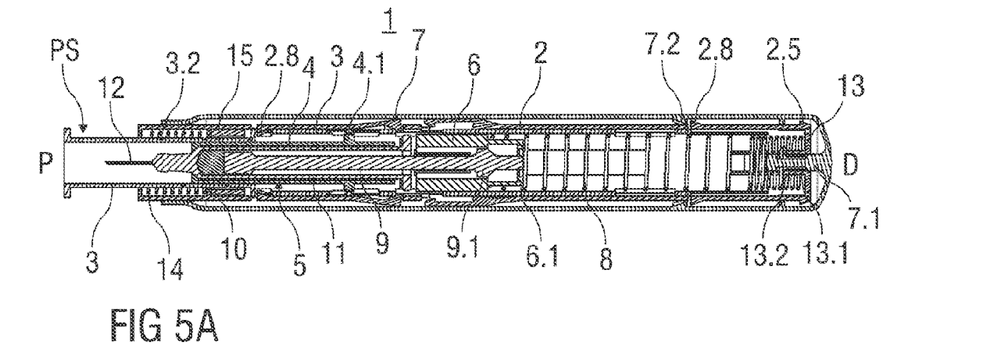
FIGS. 5A and 5B show two different sectional views of the auto-injector after uthe injection.
Figure 5B:
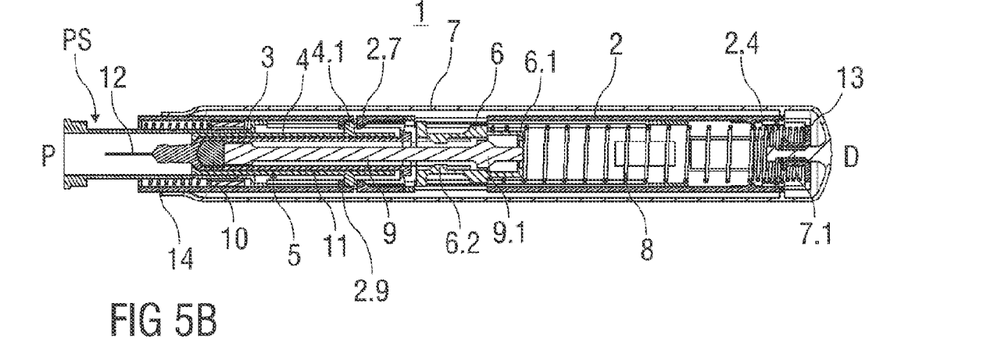

FIGS. 5A and 5B show two different sectional views of the auto-injector 1 after the injection is completed and the auto-injector 1 is removed from the injection site. The sectional plane shown in FIG. 5A extends perpendicularly to the one shown in FIG. 5B. The injection needle 12 is surrounded by the needle shroud 3 which protrudes beyond the tip of needle 12 in the safe position PS sufficiently far to avoid accidental needle stick injuries after the injection. The needle shroud 3 is permanently locked in the safe position PS by fourth clips 2.8 on the chassis 2 that latch to the needle shroud 3 after the injection is completed.

The invention claimed is:

1. Auto-injector for administering a dose of a liquid medicament (M), comprising
    a substantially cylindrical chassis arranged to contain a pre-filled syringe with a syringe barrel filled with the medicament (M), an injection needle and a stopper for sealing the syringe barrel,
    a needle shroud slidably arranged within the chassis and adapted to rest on the skin of a patient receiving an injection,
    a plunger adapted to translate the stopper to expel the dose of the medicament (M) through the injection needle,
    a coupling shroud slidably arranged within the chassis and releasably coupled to the plunger and
    a drive means capable of, upon release, driving the coupling shroud from a first position (I) in a proximal direction (P), wherein the proximal translatory movement of the coupling shroud with respect to the chassis translates the pre-filled syringe in the proximal direction (P) to expose the injection needle,
    depresses the plunger connected to the stopper into the syringe barrel to expel the dose of medicament (M) and
    advances the needle shroud to a safe position (PS) to surround the injection needle after the injection, wherein the coupling shroud is arranged to be decoupled from the plunger at a second position (II), wherein the needle shroud is arranged to prevent the decoupling of plunger and coupling shroud when the needle shroud is in a refracted position (PR), whereas the needle shroud is arranged to allow for the decoupling of plunger and coupling shroud when the needle shroud is moved from the retracted position (PR) towards the safe position (PS).

2. Auto-injector according to claim 1, characterized in that a coupling catch on the coupling shroud is arranged to abut against a shoulder formed to the plunger to releasably couple the plunger to the coupling shroud, wherein a ramped engagement of the coupling catch and the shoulder is arranged so as to allow for a deflection of the coupling catch in a radial outward direction on translating the coupling shroud with respect to the plunger in the proximal direction (P) and wherein the coupling catch abuts against the chassis in the radial outward direction so as to prevent a decoupling of the plunger and the coupling shroud until the second position (II) is reached.

3. Auto-injector according to claim 1, characterized in that the second position (II) is defined by an aperture formed into the chassis, wherein the aperture is arranged to allow the coupling catch of the coupling shroud to be deflected in the radial outward direction to decouple the plunger from the coupling shroud.

4. Auto-injector according to claim 3, characterized in that the needle shroud comprises an intermediate section that is slidably retained within the aperture, wherein the intermediate section of the needle shroud positioned in the retracted position (PR) is arranged to abut against the coupling catch in the radial direction to prevent the decoupling of the plunger from the coupling shroud.

5. Auto-injector according to claim 1, characterized in that a syringe retainer is slidably arranged with respect to the chassis that mounts the pre-filled syringe, wherein the needle shroud in the retracted position (PR) is arranged to release the syringe retainer to allow for the proximal translation of the syringe retainer carrying the pre-filled syringe with respect to the chassis to expose the injection needle.

6. Auto-injector according to claim 1, characterized in that the drive means is arranged as a single compression spring.

7. Auto-injector according to claim 1, characterized in that a manually actuatable and tubular release element is slideably arranged over the chassis and extends over a substantial length of the chassis.

8. Auto-injector according to claim 7, characterized in that the needle shroud in the retracted position (PR) is arranged to unlatch the release element to allow for a manual actuation of the release element to release the drive means.

9. Auto-injector according to claim 1, characterized in that the coupling shroud latches to a bushing attached to a distal end of the chassis to retain the coupling shroud in the first position (I).

10. Auto-injector according to claim 9, characterized in that a lug is formed to an inner surface of the release element, wherein the lug is retained in a resilient inner sleeve of the bushing to prevent a deformation of the resilient inner sleeve.

11. Auto-injector according to claim 1, characterized in that the needle shroud is slidable from an advanced position (PA) in a distal direction (D) to the retracted position (PR) and from the retracted position (PR) in the proximal direction (P) beyond the advanced position (PA) to the safe position (PS).

12. Auto-injector according to claim 1, characterized in that a rotating collar axially fixed to the chassis is arranged to engage the needle shroud in a manner that forces the rotating collar to rotate within the chassis when the needle shroud is displaced from the advanced position (PA) to the safe position (PS).

13. Auto-injector according to claim 1, characterized in that the rotating collar comprises a pin that engages a helical recess formed into the needle shroud.

* * * * *